US011714964B2

(12) United States Patent
Pajak

(10) Patent No.: US 11,714,964 B2
(45) Date of Patent: Aug. 1, 2023

(54) TEXT PROCESSING METHOD AND APPARATUS

(71) Applicant: Canon Medical Systems Corporation, Otawara (JP)

(72) Inventor: Maciej Pajak, Edinburgh (GB)

(73) Assignee: Canon Medical Systems Corporation, Otawara (JP)

( * ) Notice: Subject to any disclaimer, the term of this patent is extended or adjusted under 35 U.S.C. 154(b) by 401 days.

(21) Appl. No.: 16/818,690

(22) Filed: Mar. 13, 2020

(65) Prior Publication Data

US 2021/0286947 A1    Sep. 16, 2021

(51) Int. Cl.
G06F 40/284    (2020.01)
G06F 40/30     (2020.01)
G06N 20/00     (2019.01)
G16H 50/20     (2018.01)

(52) U.S. Cl.
CPC ............ *G06F 40/284* (2020.01); *G06F 40/30* (2020.01); *G06N 20/00* (2019.01); *G16H 50/20* (2018.01)

(58) Field of Classification Search
CPC ....... G06F 40/284; G06F 40/30; G16H 50/20; G06N 20/00; G06N 3/0454; G06N 3/08
See application file for complete search history.

(56) References Cited

U.S. PATENT DOCUMENTS 9,037,464 B1    5/2015  Mikolov et al.
9,141,916 B1 *  9/2015  Corrado ................. G06F 7/483

(Continued)

FOREIGN PATENT DOCUMENTS

CN    110968564       *  9/2018  ............ G06F 16/21
WO    WO-2016094330 A2 *  6/2016  ....... G01N 33/57423

OTHER PUBLICATIONS

Cerchiello, Paola and Nicola, Giancarlo and Rönnqvist, Samuel and Sarlin, Peter, Deep Learning for Assessing Banks' Distress from News and Numerical Financial Data (Nov. 28, 2018). Michael J. Brennan Irish Finance Working Paper Series Research Paper No. 18-15, (Year: 2018).*

(Continued)

*Primary Examiner* — Angela A Armstrong
(74) *Attorney, Agent, or Firm* — Oblon, McClelland, Maier & Neustadt, L.L.P.

(57) ABSTRACT

An apparatus comprises processing circuitry configured to pre-process text data for inputting to a trained model, the pre-processing comprising: receiving a set of text data including numerical information, the set of text data comprising a plurality of tokens, wherein a first subset of the plurality of tokens comprises tokens that do not comprise numerical information, and a second subset of the plurality of tokens comprises tokens that each comprise respective numerical information; transforming each of the plurality of tokens into a respective encoding vector, each of the plurality of tokens in the second subset having a common encoding vector; assigning a respective numerical vector to each of the plurality of tokens, wherein each token in the second subset is assigned a respective numerical vector in dependence on the numerical information in said token; and combining the encoding vectors and numerical vectors to obtain a vector representation of the text data.

17 Claims, 7 Drawing Sheets

(56) References Cited

U.S. PATENT DOCUMENTS

| | | | |
|---|---|---|---|
| 2006/0288284 A1* | 12/2006 | Peters | G06F 16/904 |
| | | | 715/700 |
| 2008/0270386 A1 | 10/2008 | Ohi et al. | |
| 2011/0196704 A1 | 8/2011 | Mansour | |
| 2019/0005019 A1 | 1/2019 | Burke et al. | |
| 2019/0273510 A1* | 9/2019 | Elkind | G06N 20/00 |
| 2021/0027167 A1* | 1/2021 | Goloubew | G06F 21/552 |

OTHER PUBLICATIONS

S. Kuang and B. D. Davison, "Numeric-Attribute-Powered Sentence Embedding," 2018 IEEE International Conference on Big Data and Smart Computing (BigComp), 2018, pp. 623-626. (Year: 2018).*

Tomas Mikolov, et al., "Efficient Estimation of Word Representations in Vector Space", arXiv:1301.3781v3, Sep. 7, 2013, 12 pages.

Jeffrey Pennington, et al., "GloVe: Global Vectors for Word Representation", Proceedings of the 2014 Conference On Empirical Methods In Natural Language Processing (EMNLP) Oct. 2014, 12 pages.

Armand Joulin, et al., "Bag of Tricks for Efficient Text Classification", arXiv:1607.01759v3, Aug. 9, 2016, 5 pages.

Yan Wang, et al., "Deep Neural Solver for Math Word Problems", Proceedings of the 2017 Conference on Empirical Methods in Natural Language Processing, Sep. 2017, 10 pages.

Ashish Vaswani, et al., "Attention Is All You Need", 31st Conference on Neural Information Processing Systems (NIPS 2017), 15 pages.

Eric Wallace, et al., "Do NLP Models Know Numbers? Probing Numeracy in Embeddings", Proceedings of the 2019 Conference on Empirical Methods in Natural Language Processing and the 9th International Joint Conference on Natural Language Processing (EMNLP-IJCNLP),Nov. 2019, 12 pages.

* cited by examiner

TEXT PROCESSING METHOD AND APPARATUS

FIELD

Embodiments described herein relate generally to a method and apparatus for text processing, for example for pre-processing medical text for inputting to a trained model.

BACKGROUND

It is known to perform natural language processing (NLP), in which free text or unstructured text is processed to obtain desired information. For example, in a medical context, the text to be analyzed may be a clinician's text note. The text may be analyzed to obtain information about, for example, a medical condition or a type of treatment. Natural language processing may be performed using deep learning methods, for example using a neural network.

In order to perform natural language processing, text may first be pre-processed to obtain a representation of the text, for example a vector representation. The representation of the text may then be input to a deep learning model.

Currently, a representation of text used for deep learning natural language processing (NLP) may be a representation that is based on embeddings. In the representation that is based on embeddings, the text is considered as a set of word tokens. A word token may be, for example, a single word, a group of words, or a part of a word. A respective embedding vector is assigned to each word token.

The embedding vector is a dense vector. The embedding vector may comprise, for example, between 100 and 1000 elements.

Embedding vectors capture semantic similarity between word tokens in a multi-dimensional embedding space. In one example, the word 'acetaminophen' is close to 'apap' and 'paracetamol' in the multi-dimensional embedding space, because 'acetaminophen', 'apap' and 'paracetamol' all describe the same medication.

In some cases, embeddings at word-piece level or at character level may be used.

The embedding vectors are used as input to a deep learning model, for example a neural network. The similarity information from the embedding vectors may allow the neural network to generalize over synonyms and closely related terms.

There are multiple known ways of learning an embedding space for words, for example Word2vec (see, for example, U.S. Pat. No. 9,037,464B1 and Mikolov, T., Chen, K., Corrado, G., & Dean, J. (2013). Efficient estimation of word representations in vector space. arXiv preprint arXiv: 1301.3781), GloVe (see, for example, Pennington, J., Socher, R., & Manning, C. (2014, October). Glove: Global vectors for word representation. In *Proceedings of the 2014 conference on empirical methods in natural language processing (EMNLP)* (pp. 1532-1543) and fastText (see, for example, Joulin, A., Grave, E., Bojanowski, P., & Mikolov, T. (2016). Bag of tricks for efficient text classification. arXiv preprint arXiv:1607.01759).

In many known methods, embeddings are only learned for a finite amount of tokens. Embeddings are learned for the tokens which occur frequently enough in a training corpus to be learned.

FIG. 1 illustrates a typical deep learning workflow for a task using text as the input. In the example of FIG. 1, the input is a passage of raw text 10. The raw text may 10 may be considered to comprise N tokens. N may be referred to as a document size.

In FIG. 1, the raw text 10 is a clinical note relating to a patient. The raw text 10 is text that has not yet been subject to any pre-processing.

The example of raw text shown in FIGS. 1, 2 and 3 reads:

"She agrees with our treatment for this patient. The patient was on aspirin 325 mg and also on Zocor 20 mg once a day. We also ordered fasting blood lipids, which showed cholesterol of 165, triglycerides 180, HDL cholesterol 22, LDL cholesterol 107."

The raw text 10 is pre-processed to obtain a representation 12 of the raw text. The representation 12 is a dense matrix of numbers comprising N multi-dimensional vectors, where N is the number of tokens in the raw text. The multi-dimensional vectors may also be referred to as embedding vectors. The embedding vectors are multi-dimensional so that they can capture semantic closeness between word tokens.

The representation 12 is used as an input for a neural network 14. The neural network 14 may be trained to produce one or more outputs 16, 18, 20, 22. For example, the neural network may be trained to produce a translation 16 of the raw text 10. The neural network may be trained to identify a set of medications 18 that have been taken by the patient in the past. The neural network may be trained to output a chance of survival 20 for the patient. The neural network may be trained to identify contraindications 22, for example contraindications for a heparin injection.

As mentioned above, embeddings may be learned for only a finite number of tokens within a set of training data. As an example, embeddings may be learned for 40000 different words. Embeddings may not be learned for words that occur very infrequently within a training text. In some circumstances, embedding may result in numerical information from the text 10 being lost.

FIGS. 2 and 3 represent known methods of dealing with numbers when embedding. FIG. 2 shows an example in which numbers are treated as words. Some numbers, for example some round numbers, may be frequent enough that an embedding is learned for them. For example, numbers that are often used for dosages (such as 10, 20, 50, 100) may appear frequently enough in a training data set for an embedding for those numbers to be learned from the training data set. Other numbers may be infrequent enough that they do not appear, or do not appear often, in the training data set. Numbers that do not appear often enough for an embedding to be learned may be treated as non-informative tokens. Non-informative tokens may also be referred to as unknown tokens. In some methods, non-informative tokens may be assigned a vector of all zeros.

In the example shown in FIG. 2, two numbers 30 in the text 10 are frequent enough to have a learned embedding. The numbers 30 having an embedding are 325 and 20. Four other numbers 32 do not have a learned embedding. The numbers 32 that do not have a learned embedding are 165, 180, 22 and 107.

The numbers that do not have a learned embedding are treated as non-informative unknown tokens. The raw text 10 may be considered to be transformed into a new text 34 in which the numbers that do not have a learned embedding are replaced by an indicator 36 of an unknown token. An embedding matrix 38 is obtained. In the embedding matrix, unknown tokens 36 are assigned a vector of zeros.

Some understanding of number order may be present or emergent in a model trained using an embedding in which numbers are treated as words. However, the understanding will only extend to a limited range of numbers, for example only to the numbers that have learned embeddings.

FIG. 3 shows a different method of dealing with numbers. In the example of FIG. 3, all of the numbers 30, 32 in the raw text 10 are treated equally and are simply discarded. The raw text 10 may be considered to be transformed into a new text 40 in which all numbers are omitted. An embedding matrix (not shown) may be obtained in which all numbers are treated as unknown tokens.

The methods of FIGS. 2 and 3 each result in a loss of numerical information that is present in the raw text 10. In some circumstances, the lost information could have been useful for the task to be performed by a neural network into which the text is to be input. For example, numerical information about cholesterol levels could have been useful for predicting a presence of contraindications to a procedure that requires a normal level of cholesterol. Numerical information about measurements could have been useful for detecting a drop in measurements between 2 time points.

Even the embedding vectors for common numbers in the method of FIG. 2 will not represent arithmetical similarity and/or ordering of the numbers.

BRIEF DESCRIPTION OF THE DRAWINGS

Embodiments are now described, by way of non-limiting example, and are illustrated in the following figures, in which.

DETAILED DESCRIPTION

Certain embodiments provide an apparatus comprising processing circuitry configured to pre-process text data for inputting to a trained model, the pre-processing comprising: receiving a set of text data including numerical information, the set of text data comprising a plurality of tokens, wherein a first subset of the plurality of tokens comprises tokens that do not comprise numerical information, and a second subset of the plurality of tokens comprises tokens that each comprise respective numerical information; transforming each of the plurality of tokens into a respective encoding vector, each of the plurality of tokens in the second subset having a common encoding vector; assigning a respective numerical vector to each of the plurality of tokens, wherein each token in the second subset is assigned a respective numerical vector in dependence on the numerical information in said token; and combining the encoding vectors and numerical vectors to obtain a vector representation of the text data.

Certain embodiments provide a method of pre-processing text data for inputting to a trained model, the method comprising: receiving a set of text data including numerical information, the set of text data comprising a plurality of tokens, wherein a first subset of the plurality of tokens comprises tokens that do not comprise numerical information, and a second subset of the plurality of tokens comprises tokens that each comprise respective numerical information; transforming each of the plurality of tokens into a respective encoding vector, each of the plurality of tokens in the second subset having a common encoding vector; assigning a respective numerical vector to each of the plurality of tokens, wherein each token in the second subset is assigned a respective numerical vector in dependence on the numerical information in said token; and combining the encoding vectors and numerical vectors to obtain a vector representation of the text data.

Figure 4:
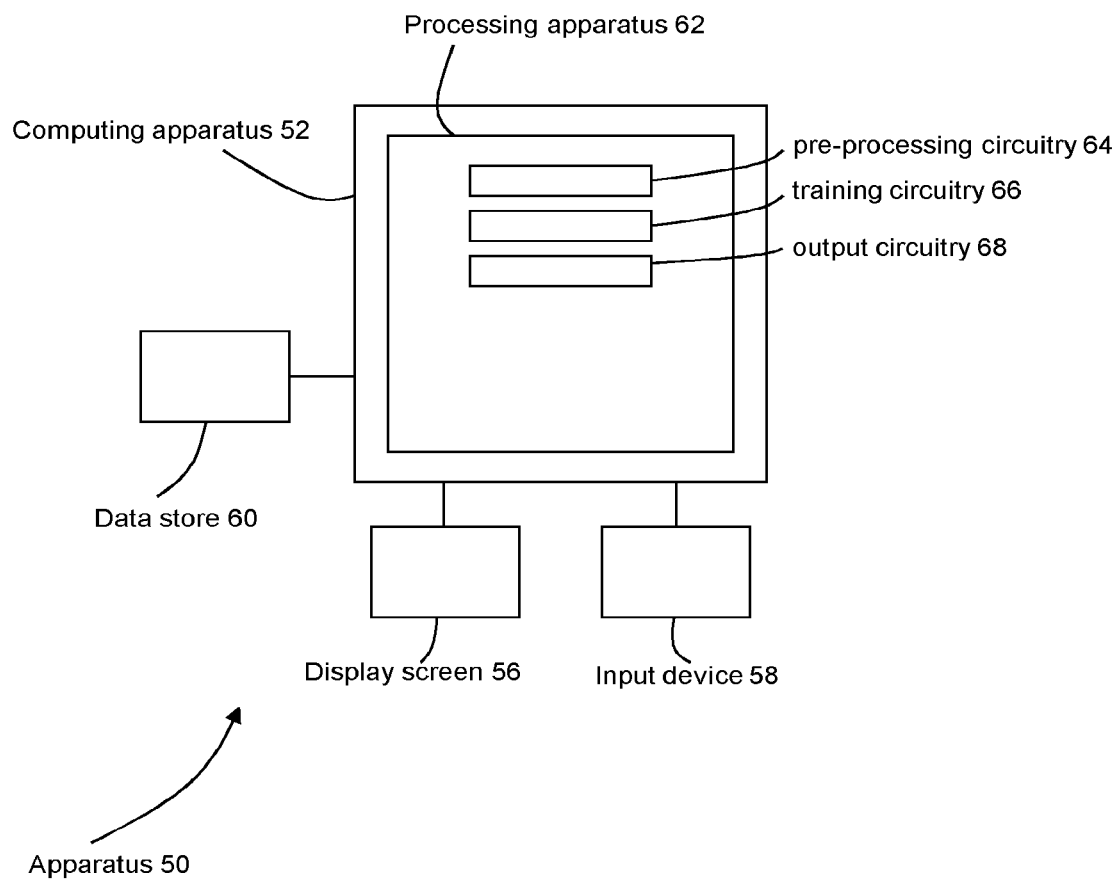
FIG. 4 is a schematic illustration of a text processing apparatus in accordance with an embodiment.

A text processing apparatus 50 according to an embodiment is illustrated schematically in FIG. 4. In the present embodiment, the text processing apparatus 50 is configured to process medical text. The medical text may comprise, for example, clinical notes. In other embodiments, the text processing apparatus 50 may be configured to process any appropriate text.

The text processing apparatus 50 comprises a computing apparatus 52, which in this case is a personal computer (PC) or workstation. The computing apparatus 52 is connected to a display screen 56 or other display device, and an input device or devices 58, such as a computer keyboard and mouse.

The computing apparatus 52 receives medical text from a data store 60. In alternative embodiments, computing apparatus 52 receives medical text from one or more further data stores (not shown) instead of or in addition to data store 60. For example, the computing apparatus 52 may receive medical text from one or more remote data stores (not shown) which may form part of a Picture Archiving and Communication System (PACS) or other information system.

Computing apparatus 52 provides a processing resource for automatically or semi-automatically processing medical text data. Computing apparatus 12 comprises a processing apparatus 62. The processing apparatus 62 comprises pre-processing circuitry 64 configured to pre-process text to obtain a representation of the text; embedding training circuitry 65 configured to train an embedding; model training circuitry 66 configured to train a model; and text processing circuitry 67 configured to input a representation of text to the trained model to obtain one or more outputs.

In the present embodiment, the circuitries 64, 65, 66, 67 are each implemented in computing apparatus 52 by means of a computer program having computer-readable instructions that are executable to perform the method of the embodiment. However, in other embodiments, the various circuitries may be implemented as one or more ASICs (application specific integrated circuits) or FPGAs (field programmable gate arrays).

The computing apparatus 52 also includes a hard drive and other components of a PC including RAM, ROM, a data bus, an operating system including various device drivers, and hardware devices including a graphics card. Such components are not shown in FIG. 4 for clarity.

The text processing apparatus 50 is configured to train an embedding model; to use the trained embedding model to pre-process text to obtain a representation of the text that comprises a set of extended embedding vectors; to train a neural network to obtain one or more desired outputs from a set of extended embedding vectors; and to apply the neural network to pre-processed text to obtain the one or more desired outputs. In other embodiments, a different apparatus may be used to perform the training of the embedding model and/or the training of the neural network. In further embodiments, in further embodiments, any suitable combination of apparatuses may be used to perform any of the steps described below with reference to FIGS. 5, 7 and 8.

Figure 5:
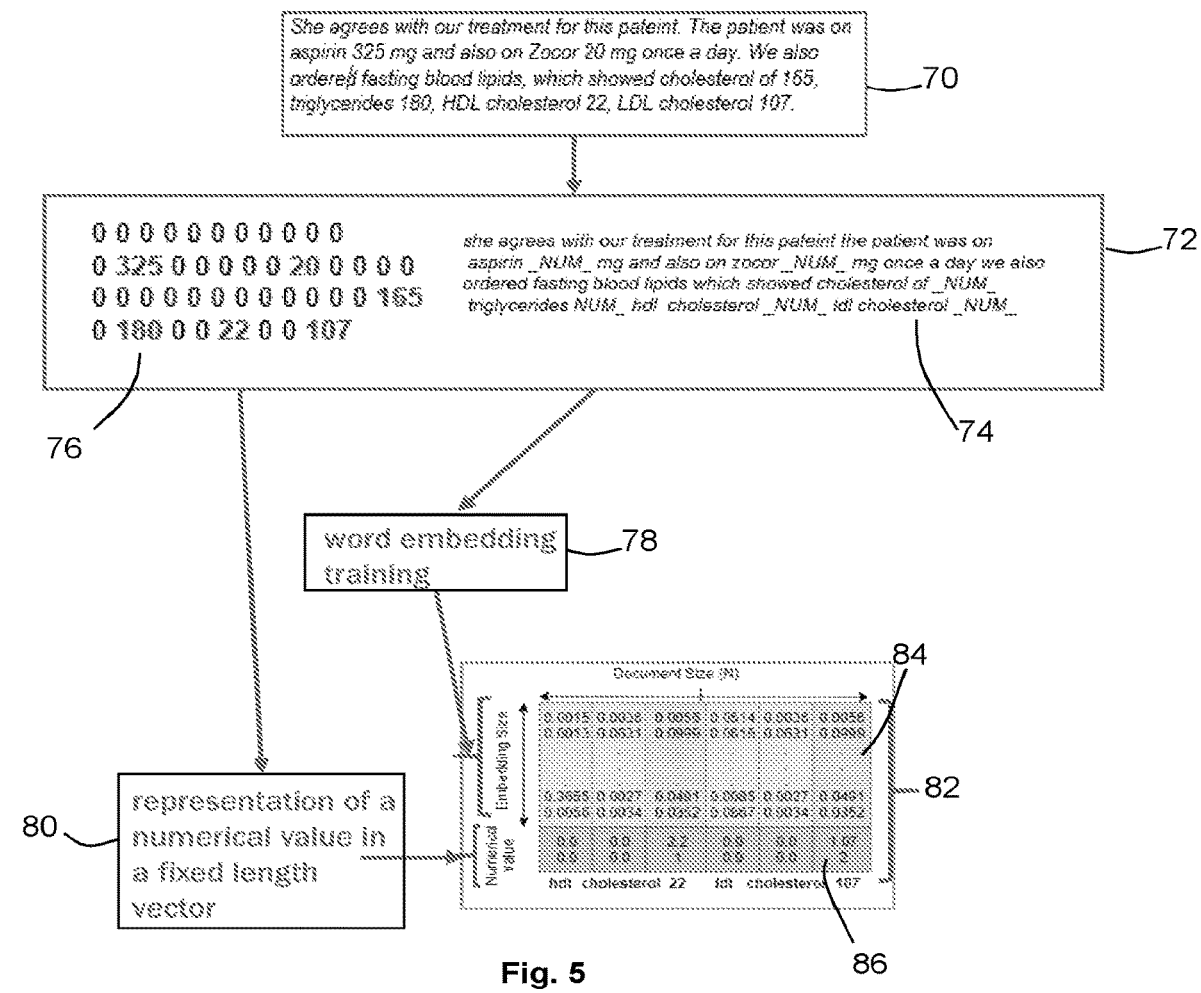
FIG. 5 is a flow chart illustrating in overview a method of training a model to pre-process text data in accordance with an embodiment.

FIG. 5 is a flow chart illustrating in overview a training method in accordance with an embodiment. At the start of the training method, the pre-processing circuitry 64 receives training text 70 for training a word embedding. The training text 70 may comprise raw text relating to a large number of patients or other subjects. For example, the training text 70 may comprise tens of thousands of text samples, or more. The training text 70 may relate to tens of thousands of subjects, or more.

Figure 1:
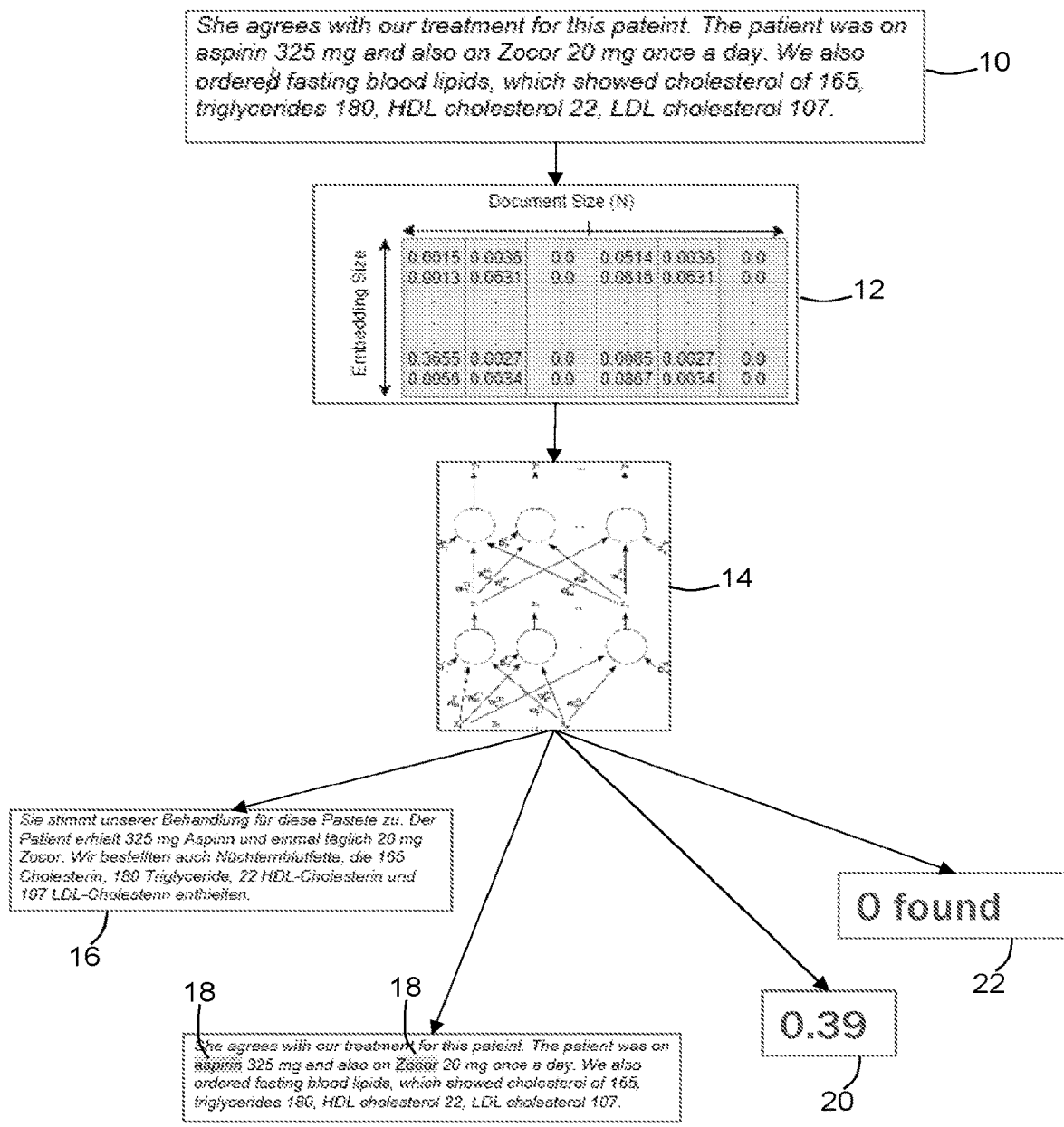
FIG. 1 is a flow chart illustrating in overview a method for obtaining a representation for text and processing the representation using a neural network to obtain one or more outputs.
Figure 2:
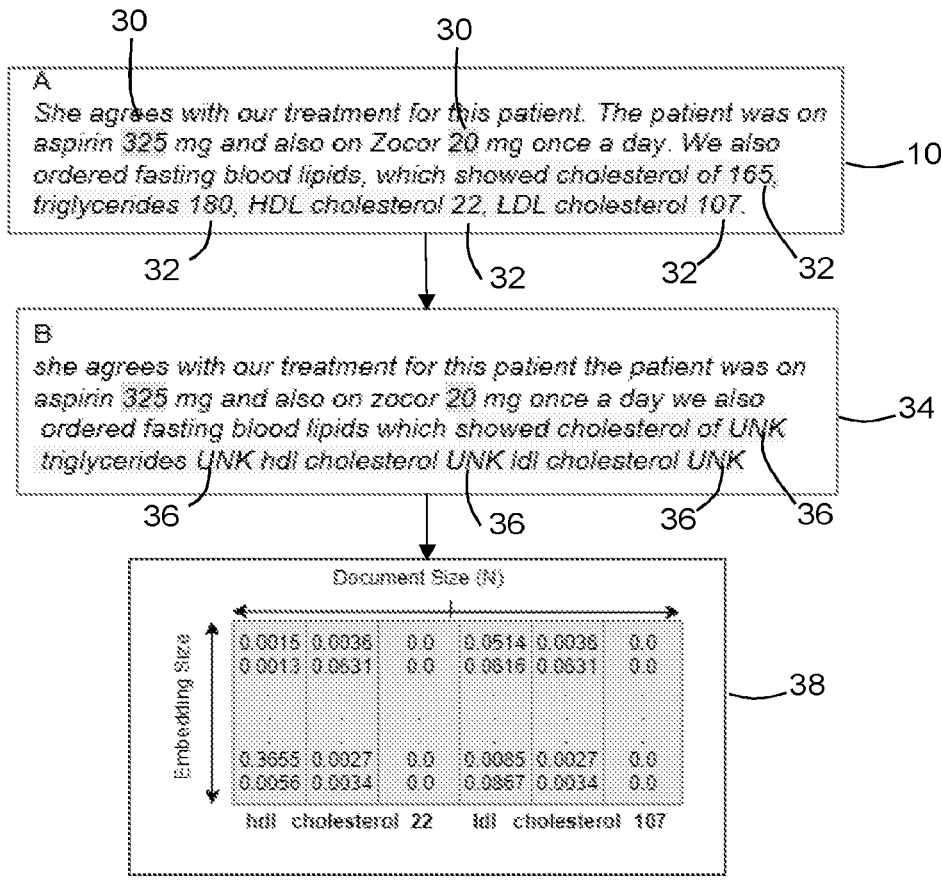
FIG. 2 is a flow chart illustrating in overview a method for representing numbers in text using embedding vectors.
Figure 3:
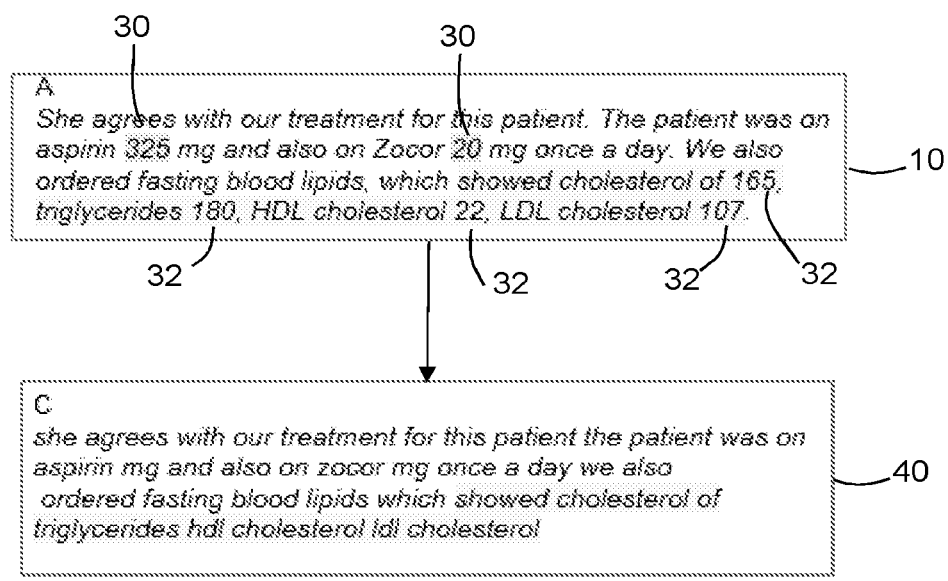
FIG. 3 is a flow chart illustrating in overview a method in which numbers are removed from text during pre-processing.

In FIG. 5, the training text 70 is represented by the same text as was used to represent the raw data 10 in FIGS. 1 to 3. However, in practice, the training text 70 comprises large quantities of medical text. The resulting trained embedding may be applied to any medical text, including medical text that is not part of the training text 70.

The pre-processing circuitry 64 divides the training text 70 into a set of tokens, each of which comprises a respective word or number. At stage 72, the pre-processing circuitry 64 assigns a number token to each of the numbers in the training data 70 to obtain a new text 74. In the new text, the same number token is assigned to each of the tokens in the original text 70 that comprises a number. The number token that is assigned does not depend on a value of the number. Instead, the same number token is common to all numbers.

The pre-processing circuitry 64 assigns a numerical value to each token in the training text 70. Each token in the training text 70 is assigned a respective numerical value. Numerical values are assigned to tokens that comprise words as well as to tokens that comprise numbers.

In the embodiment of FIG. 5, the pre-processing circuitry 64 assigns a numerical value of zero to every token that comprises a word. In other embodiments, any suitable numerical value may be assigned to tokens that comprise words. In some embodiments, a common default numerical value is assigned to every token that comprises a word. In some embodiments a NAN (not a number) value is assigned to every token that comprises a word.

For each token that comprises a number, the pre-processing circuitry 64 assigns the value of that number as the numerical value for the token. Any numerical values may be assigned. The numerical values are not restricted to a limited set of numbers, for example those in a dictionary.

An output of the assigning of numerical values is an array of numerical values 76 whose length corresponds to the number of tokens in the training text 70.

At stage 78 of FIG. 5, the embedding training circuitry 65 performs a word embedding training. Any suitable method of word embedding training may be used, for example Word2vec, GloVe or fastText. A word embedding model learns an embedding for the words in the version 74 of the training text 70 in which numbers are replaced by a common number token.

By passing the text 74 through a word embedding model during training or inference, the tokens are represented as embeddings of fixed length. Each number is represented by the same embedding vector, because the numbers are represented by the same number token in the text 74. In other embodiments, any suitable method may be used to obtain a common embedding token for all of the numbers.

An output of the word embedding training at stage 78 is an embedding model that is trained to convert a text into a set of embedding vectors. A further output of stage 78 is a set of embedding vectors 84 for some or all of the training text 70.

At stage 80, the pre-processing circuitry 64 represents each of the numerical values in the array 76 as a respective fixed length vector 86.

Figure 6:
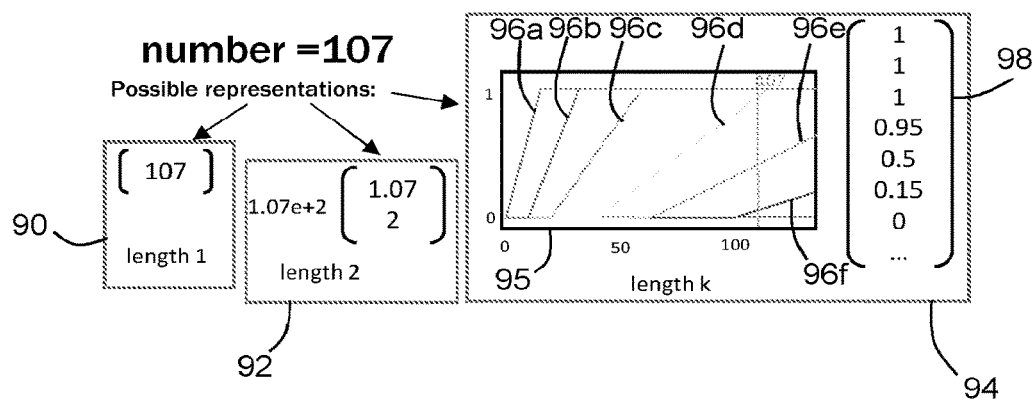
FIG. 6 illustrates three possible representations of a numerical value.

FIG. 6 illustrates several possible ways in which a numerical value can be represented. The number 107 is used in FIG. 6 as an example of a number to be represented. Three possible representations 90, 92, 94 are shown in FIG. 6. In the first representation 90, the number is represented as a vector of length 1. The vector contains the value (in this case, 107) of the number itself.

In the second representation 92, the number is represented as a vector of length 2. The vector comprises the mantissa and the exponent of the number. The second representation 92 may better capture the dynamic range of numbers than the first representation 90. In the case of the number 107, the number may be represented as 1.07e+2. The values in the vector of length 2 are therefore 1.07 and 2.

In the third representation 94, the number is represented as a vector 98 using a set of functions 96, which in the present embodiment is a set of k weakly monotonic functions capturing different overlapping dynamic ranges. A plot 95 in FIG. 6 represents some of the functions 96 as lines 96a, 96b, 96c, 96d, 96e, 96f. The ranges of the functions overlap. It may be seen that a line 97 representing the number (in this case, 107) intersects several of the functions 96d, 96e, 96f. The intersection points of the number with the functions 96 are used to form the vector 98. In some circumstances, representing the number by the points at which it cuts through a set of monotonic increasing function may better capture dynamic range than some other representations.

In further embodiments, numbers may be represented by any representation that captures the natural ordering of numbers and that allows operations of addition and subtraction to be approximated. For example, any suitable set of k functions may be used to represent numerical information as a vector of length k.

The pre-processing circuitry 64 extends each of the embedding vectors obtained at stage 78 by the representation of the numerical value of the token to which the embedding vector relates. In the embodiment shown in FIG. 5, each of the numerical values is represented as a vector of length 2 having a mantissa and exponent.

The pre-processing circuitry 64 produces an output 82 comprising a respective extended embedding vector for each of the tokens in the training text 70. Each extended embedding vector comprises an embedding vector 84 which has been extended by a fixed length representation 86 of a numerical value. The numerical values of numerical tokens are included explicitly in the embedding vector.

In some circumstances, the extended embedding vectors retain numerical information that may have been lost in a conventional embedding method (for example, methods described above with reference to FIGS. 1 to 3).

Figure 7:
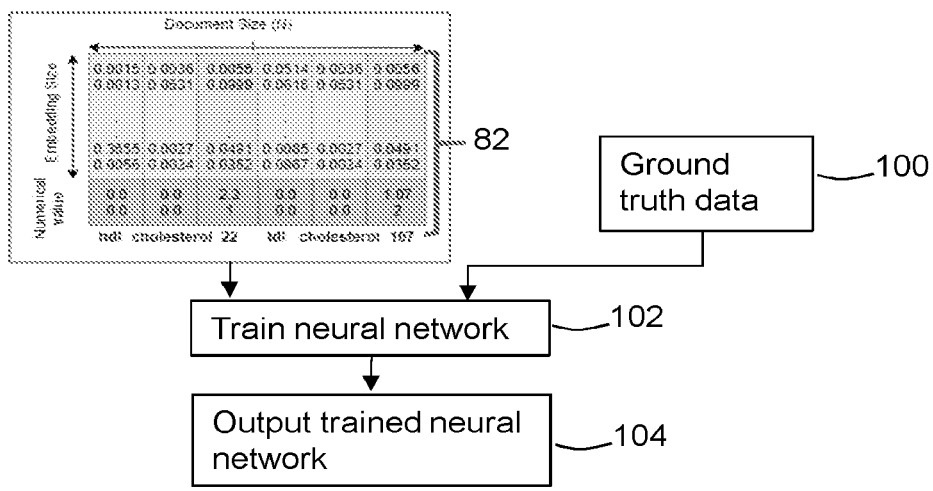
FIG. 7 is a flow chart illustrating in overview a method of training a neural network to process text.

FIG. 7 is a flow chart illustrating in overview a method of training a neural network to process text. The model training circuitry 66 receives a representation of the training text 70, which comprises a set of extended embedding vectors 82 for the training text 70. In the present embodiment, the model training circuitry 66 also receives a set of ground truth data 100. For example, the ground truth data 100 may comprise a set of structured data that represents information that is also contained within the raw training text 70. In other embodiments, model training may be performed without ground truth data.

At stage 102, the model training circuitry 66 performs a training process in which a model is trained to produce a desired output using the representation 82 of the training data 70. In the present embodiment, the model comprises a neural network. In other embodiments, any suitable model may be used, for example any suitable deep learning model. The model may comprise a deep learning algorithm. The trained model may comprise a neural network, for example a convolutional neural network (CNN), a recurrent neural network (RNN), a densely connected network, a transformer language model, or an architecture combining any of the above. In other embodiments, the model may comprise any suitable form of machine learning, for example a support-vector machine (SVM) or a random forest. In further embodiments, the model may not be a deep learning model. The model may be any model that takes as an input the representation comprising extended embedding vectors.

The desired output may comprise, for example, a translation of the text 70; a set of medications taken by the patient in the past; a chance of survival; or an identification of contraindications. The desired output may comprise an assessment of whether a value is within a predetermined range. The desired output may comprise an assessment of whether a value has changed over time. The desired output may comprise a free-text answer to a question posed in natural language, wherein the free-text answer is based on the text 70. The desired output may comprise an abstracted summary of a longer text 70 which preserves the sense of the original text 70. The trained model may be used for text mining, for example for processing large volumes of text.

At stage 104, the model training circuitry 66 outputs a trained model. The model has been trained to receive a representation of text and to output the desired output.

Figure 8:
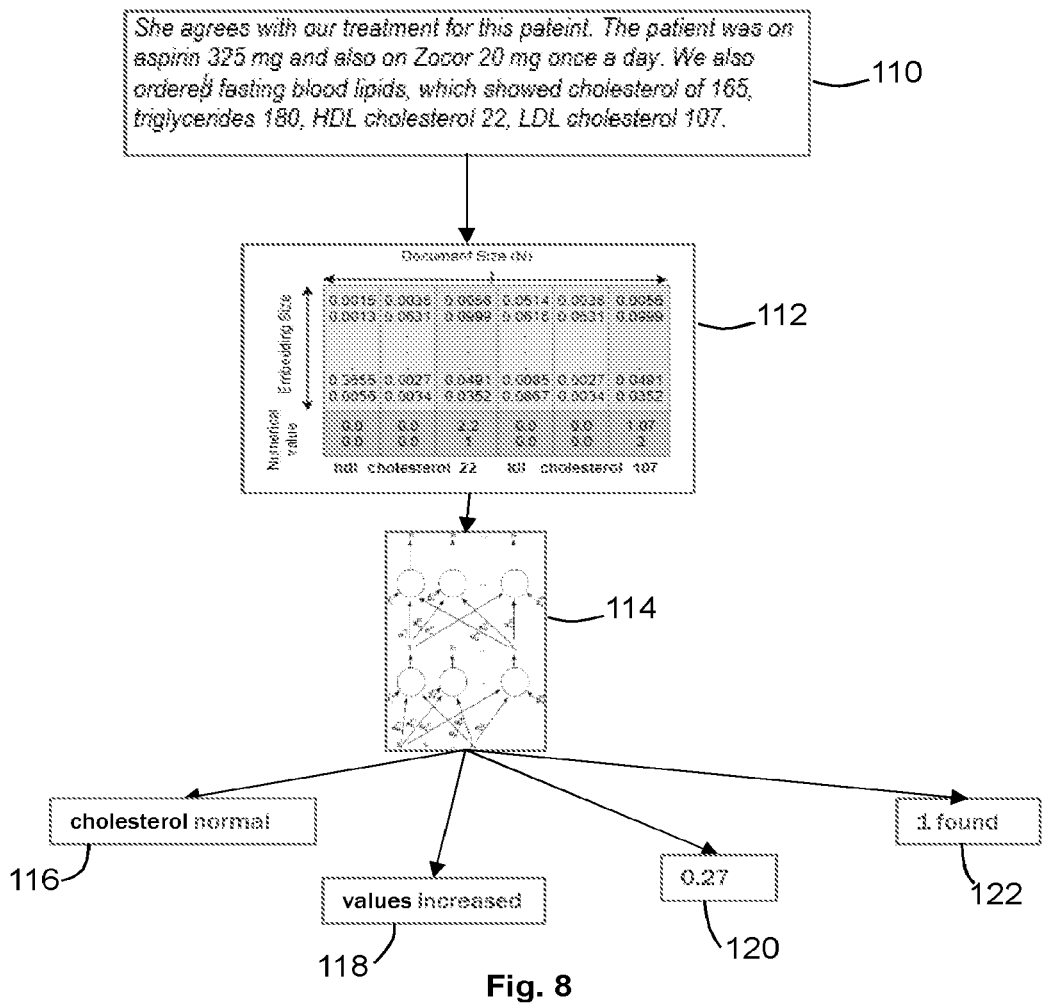
FIG. 8 is a flow chart illustrating in overview a method for obtaining a representation for text and processing the representation using a neural network to obtain one or more outputs, in accordance with an embodiment.

FIG. 8 illustrates in overview a method of applying a trained neural network to obtain a desired output. The pre-processing circuitry 64 receives a passage of raw text 110, which may also be described as text data or input text. In the present embodiment, the raw text 110 is also displayed on display screen 56.

The pre-processing circuitry 64 pre-processes the raw text 110 to obtain a representation 112 of the raw text 110, which in the present embodiment is a set of extended embedding vectors 112.

The pre-processing comprises replacing each of the numbers with a common number token and applying the trained embedding models to obtain a set of embedding vectors. The pre-processing further comprises obtaining an array of numerical values as described above with reference to FIG. 5, and extending the embedding vectors with the numerical values.

The text processing circuitry 67 uses the representation 112 as an input for the trained neural network 114. In the embodiment shown in FIG. 8, the neural network 114 is trained to produce four outputs 116, 118, 120, 122. The text processing circuitry 67 displays the output display screen 16.

The neural network 114 is trained to provide a determination 116 of whether a cholesterol level is within a normal range. The neural network 114 is trained to provide a determination 118 of whether one or more values have changed after treatment, for example whether values have increased. The neural network 114 is trained to output a chance of survival 120. The neural network 114 is trained to output any contraindications 112.

In other embodiments, the neural network 114 may be trained to produce any suitable outputs. The neural network 114 may be trained to compare numerical values to each other, with an interval, or with one or more target values. The neural network 114 may be trained to put numerical values 114 in numerical order.

Pre-processing the text 110 in such a way that numerical information is retained may allow outputs to be obtained that would not have been available using other representations. For example, in representations in which numerical information is discarded, it may not be possible to obtain information about whether a value is within a normal range, or whether a value has increased. A representation in which numerical values are retained may allow numerical values to be compared with each other, with an interval, or with one or more target values. The model may learn to approximate numerical operations.

Pre-processing the text 110 in such a way that numerical information is retained may improve the accuracy of some outputs. For example, an improved estimate of a chance of survival may be provided. In the embodiment shown in FIG. 8, the chance of survival is 0.27, whereas in FIG. 1 it was 0.38 for the same input data. The value in FIG. 8 may be more accurate.

Improved information about contraindications may be provided. For example, in FIG. 8 one contraindication is found. In the method of FIG. 1, no contraindication was found from the same input data.

The method of FIG. 8 may be used to provide clinical decision support for any suitable disease or condition. Information retrieval may be driven by a smart relevancy engine implementing the method of FIG. 8.

The text processing circuitry 67 may use outputs from the neural network 114 to automatically point out information that is important for a clinical workflow. In training, the neural network 114 may automatically discover what information is important for a given clinical workflow. The neural network 114 may learn subtle dependencies between numbers, for example dependencies between numbers occurring at different places in a clinical note. In some circumstances, dependencies between numbers at different places within a clinical note may be easily overlooked by a clinician reading through text. A human may only pay attention to one spot within the text. An algorithm, for example a deep learning algorithm, may discover dependencies in the whole text.

The neural network 114 may be trained to classify documents with codes to present a summarized history of the patient. For example, the codes may be codes for symptoms, diseases and/or procedure. The neural network 114 may be configured to produce a summary in which abnormal numbers or combinations of numbers are highlighted. In some embodiments, numbers that are determined to be normal may be omitted from the summary.

Knowledge may be generated based on the medical history of other patients. The neural network 114 may be trained to perform prediction and/or prescription based on training data. For example, the neural network may use information from similar patients in the past who have had a positive outcome from a treatment.

Allowing a model to learn to approximate mathematical operations may provide a scalable method for processing text, and in particular for processing free text. In practice, there will be a variety of ways of phrasing the same information in text, for example in clinical notes. In some circumstances, a rule-based method of processing the text, for example by using templates, may not scale to the different possible ways of wording the information. A neural network method may scale with minimal human intervention if it is provided with enough training data.

In medical records, it may often by the case that plenty of numerical information is available in free text. In some cases, the numerical information may be duplicated elsewhere in a structured way. However, in some circumstances, access to the structured data may be more difficult. For example, unstructured free text data may be stored in a separate system from structured numerical information. In some circumstances, a number stored as structured data may lack text context. By using methods as described above, the text context of a number may be used to add meaning to the number through deep learning training. For example, the words surrounding a number may be used to impart meaning to that number.

In free text, it may often be the case that numbers are presented without any comment on their significance. For example, a body temperature may be reported as 39 C without any comment saying that 39 C is an abnormally high body temperature. It is assumed by the writer of the document that a person reading the document will know that 39 C is an abnormally high body temperature. In this case, numerical information may provide information that cannot be gained from only the surrounding text. If an attempt were made to classify the document with symptom or disease labels without access to the numerical information, the abnormal body temperature could be missed. By using the numerical information in the text, additional information may be obtained beyond that available from the words alone.

A method as described above in relation to any of FIGS. 5, 7 and 8 may be used for processing of any suitable medical data, for example, laboratory data, symptom data, vital signs data, dosage data, measurement data or genomic data.

A method as described above in relation to any of FIGS. 5, 7 and 8 may be used in many different medical contexts. Some examples of such medical contexts are provided below.

In some embodiments, the neural network 114 is trained to detect a direction of change of a parameter that is mentioned in text, for example in clinical notes. The parameter may comprise, for example, a laboratory measurement or a medication dose. The neural network 114 may be trained to learn the mathematical operation $x < y$, where $x$ and $y$ are both numerical values that are present in the text.

In some embodiments, the neural network 114 is trained to determine whether a value for a parameter is normal or abnormal. For example, the parameter may be a laboratory result that is included in clinical notes. In some embodiments, the neural network 114 may be trained to determine whether the value is normal or abnormal without an explicit context of what the normal range is. The range and comparison may be learned from training data. The neural network may be trained to learn the mathematical operation $x < \text{constant\_A}$, $x > \text{constant\_B}$ where $x$ is in the text.

The neural network 114 may be trained to determine whether a number is within any appropriate interval. In some circumstances, the interval may be variable. The interval may depend on contextual information in the text.

In some embodiments, the neural network 114 may be trained for implicit learning of the predictive value of a combination of parameter values (for example, measurements and/or doses) for a given health outcome. Any suitable mathematical formula may be approximated by the neural network 114.

In some embodiments, the neural network 114 may be trained to highlight numerical information that is relevant to a decision-making process. Relevant information may be highlighted using any appropriate attention mechanism. For example, a part of the raw text 110 may be highlighted using a color, font type, box, or arrow. A cursor or scroll position may be changed to draw a user's attention to the relevant information in the raw text 110. The highlighting may show a user what numbers the algorithm is paying attention to. Implicit learning from numbers may become exposed to the user, to explain to the user the basis for the neural network's outputs.

In some embodiments, while a user is taking free-form clinical notes, the input of the user can be validated by the neural network 114. The neural network 114 may compare numbers to normal or abnormal ranges as the numbers are typed. Mistyped numbers may be captured using the neural network 114. Mistyped numbers may be highlighted in any suitable manner. Hints may be displayed to the user. For example, a text box may appear on display screen 56 with a text saying 'Are you sure you meant Paracetamol 5000 mg daily?'

A method according to any of FIGS. 5, 7 and 8 may also be used for processing of non-medical text. The text may be any text that contains numerical information, for example any free-form or unstructured text notes. For example, the text may be financial text. A representation of the financial text may be generated in which numerical information is retained. A model may be trained to obtain outputs from the financial text, for example to obtain relationships between different numbers in the financial text or to compare numbers to each other, to intervals, or to targets. In other embodiments, the text may comprise other forms of free text reports, for example industrial reports about the inspection of machinery.

In embodiments described above with reference to FIGS. 5, 7 and 8, tokens are represented by dense embedding vectors which capture semantic similarity of the tokens. In other embodiments, any other vector representation of word or word-piece tokens may be used. The vector representation may comprise a sparse or dense vector of any length. In some embodiments, the vector representation captures semantic similarity of the tokens. In other embodiments, the vector representation may not capture semantic similarity of the tokens. For example, the vector representation may be obtained by sparse one-hot encoding.

A simple prototype in accordance with an embodiment was developed to demonstrate a type of task that may be facilitated by using a representation that retains numerical information. In the prototype, a model was given a simplified task of detecting a direction of difference between values.

A plurality of samples of training text were generated. The training text may also be referred to as input text. The samples of text were each in the following format:

random sentences+blood glucose level changes from {num_A} mg dl to {num_B} mg dl+random sentences where numerical values were used in place of num_A and num_B.

Each sample in which num_A>num_B was classified as a decrease. Each sample in which num_A>num_B was classified as an increase.

The model was trained on the samples of training text. The model was trained with the aim of the model learning to classify the samples as increases or decreases. The model was not provided with any classification of the samples.

Two training conditions for the model were used. The two training conditions are represented by FIG. 9 and FIG. 10 respectively.

Figure 9:
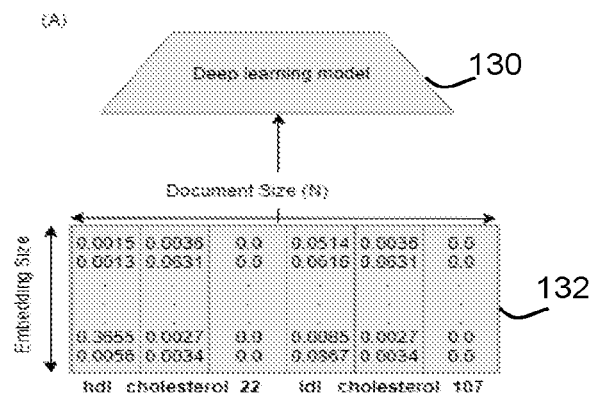
FIG. 9 is a schematic illustration of inputting embedding vectors into a deep learning model.

In the first training condition as represented in FIG. 9, the word tokens in the input text were represented as standard word2vec embeddings. A representation 132 of the input text as word2vec embeddings was used to train a deep learning model 130.

Figure 10:
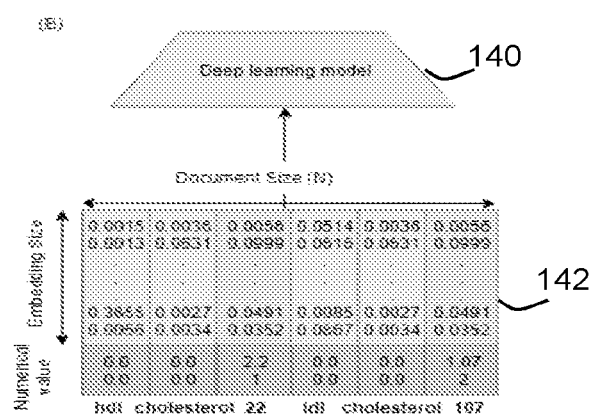
FIG. 10 is a schematic illustration of inputting extended embedding vectors into a deep learning model in accordance with an embodiment.

In the second training condition as represented in FIG. 10, the word2vec embeddings were extended with numerical information to obtain extended embedding vectors as described above with reference to FIG. 5. Numbers were replaced with a common number token before embedding as described above with reference to FIG. 5. The numerical information was represented by vectors of length 2, comprising mantissa and exponent. A representation 142 of the input text as extended embedding vectors was used to train a deep learning model 140.

In the prototype, the model 130, 140 was a convolutional neural network with attention mechanism for multilabel classification of variable length text.

Figure 11:
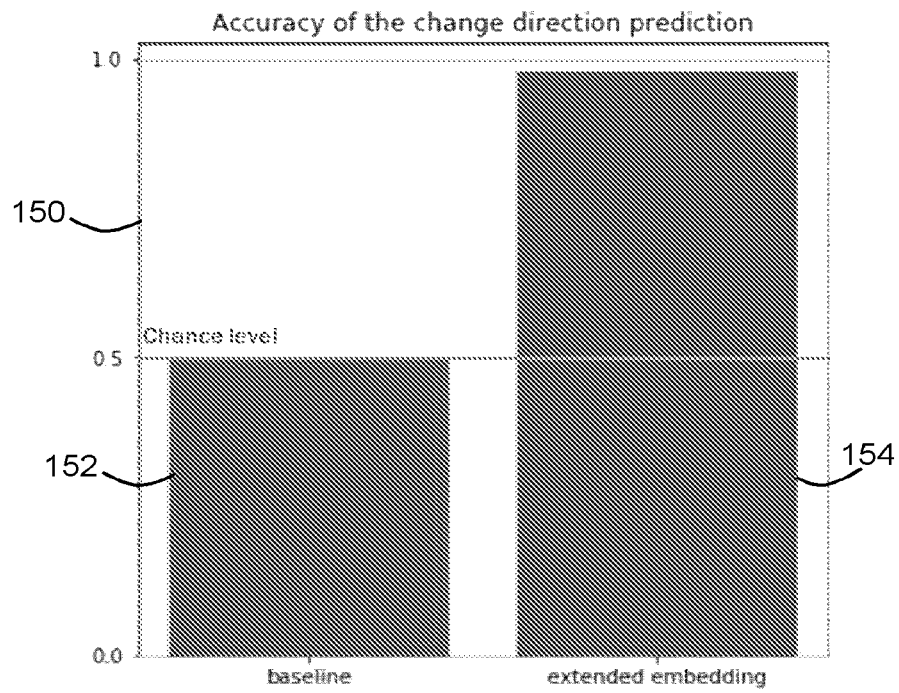
FIG. 11 is a plot showing results of a prototype, the results comprising accuracy of a change direction prediction.

Results of the prototype are illustrated in the plot 150 of FIG. 11. The results indicate an accuracy of the model's classifying of the samples as increases or decreases.

For the standard embeddings (model 130, bar 152 of FIG. 11), results of the classifying as increases or decreases were at chance level (50% accuracy). Numerical information was not available to the model.

For the extended embeddings (model 140, bar 154 of FIG. 11), accuracy of 98% was achieved.

Figure 12:
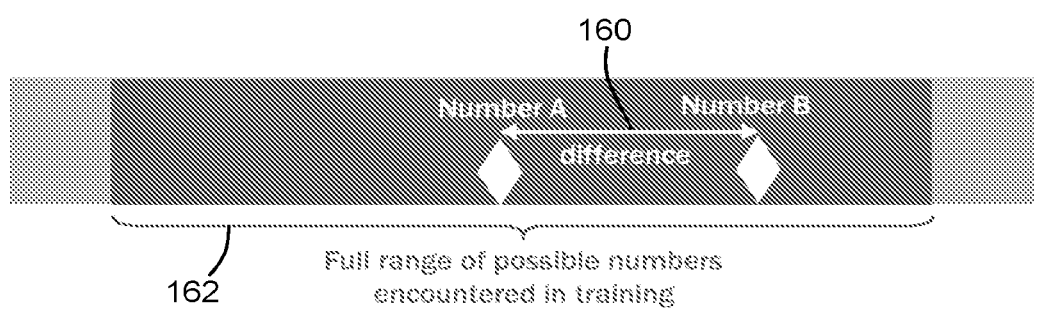
FIG. 12 is a schematic illustration of a difference between two numbers.

FIG. 12 represents a difference 160 between a number A and a number B. The difference 160 is a proportion of a full range 162 of possible numbers that were encountered in training.

In the prototype, it was found that a correct classification was possible as long as the minimum difference between the numbers was greater than 6% of the available range 162 of numbers to sample from. Notes with numbers that were close to each other in value were the most likely to be misclassified.

The prototype shows that the presence of numerical information in the representation may allow tasks to be performed that may not be possible using representations in which numerical information is discarded.

In some circumstances, accuracy of the prototype may be improved across larger ranges 162 and/or smaller differences 160 by using a more complex representation of the numerical information.

It is noted that the task for which the prototype model was trained is capable of being solved using a rule-based method based on pattern matching and predetermined task-specific logic. However, the rule-based template may not scale well when considering a free text input in which the same information may be represented in many different ways. A neural network may be trained to obtain a mathematical operation from many different possible phrasings.

In embodiments described above, the representation used to represent text comprises a respective extended embedding vector for each word or number. In other embodiments, the representation may comprise a respective extended embedding vector for each of a plurality of tokens within the free text. Each token may be, for example, a word, a part of a word (which may be of any length), a group of words, a number, a symbol (for example, a punctuation mark) or any combination, for example a combination of one or more numbers with one or more words. The embodiments described above may be performed using word-piece tokenization.

In further embodiments, any suitable representation may be used that retains numerical information for each token.

In still further embodiments, the text processing circuitry 67 does not make use of a representation as described above, for example a representation in which tokens are represented by extended embedding vectors. A contextualized semantic meaning of each number is learned from contextual information in tokens around the number, for example from a sentence around it. The value of the number may be passed straight through to provide inference in a separate system. The value of the number may be passed to another algorithm that makes use of the value.

Certain embodiments provide a natural language processing algorithm, learning from training data examples, to output information which relies on numerical information in the unstructured text.

1.1. A neural network architecture representing tokens in the input text as dense embedding vectors with the representation of the numerical value of each token appended to the embedding vector for each token.

1.2 Representation of token's numerical value occupying a fixed length vector of any length greater than 0, and capturing natural ordering of numbers.

1.3 The dependency on numerical values is learned from training data, not predetermined with rules or templates.

A natural language processing algorithm may be provided without representation described in 1.1 and 1.2, where the meaning of the number is learned exclusively from the context tokens and the value of the number is passed straight through to perform inference in a separate system.

Representation of token's numerical value may be specifically a vector of length 1 containing the number itself.

Representation of token's numerical value may be specifically a vector of length 2 containing the coefficient and exponent of the exponential notation.

Representation of token's numerical value may be a vector of length k formed by applying k weakly monotonic functions with overlapping dynamic ranges to the number.

The algorithm may perform the task of comparing 2 numbers mentioned in the unstructured clinical text.

The algorithm may perform the task of determining whether a number mentioned in the unstructured clinical text belongs to an interval. The interval may be variable and depend on the other context information in the text.

Certain embodiments provide an apparatus for processing a natural language data set comprising processing circuitry configured to: obtain a pre-processed data set by: assigning a common number token to each number in the natural language data set, wherein the common number token is a fixed indicator that does not depend on the value of each number; assigning a respective numerical value to each token in the natural language data set, wherein the numerical value is zero or null or a default value if the token is not a number, and the numerical value comprises or is based on the value of the number if the token is a number; perform an embedding procedure on the tokens of the pre-processed data set to obtain respective embedding vectors for at least some of the tokens; for each of the embedding vectors, obtain an extended embedding vector by appending a representation of the numerical value assigned to the token for that embedding vector to obtain an extended embedding vector; and use a trained model to process the extended embedding vectors to obtain a desired output.

The trained model may comprise a neural network.

The representation of the numerical value may comprise a fixed length vector. The representation may capture the natural ordering of numbers.

The representation of the numerical value may comprise a vector of length 1 containing at least one of the number itself, the numerical value. The representation of the numerical value may comprise a vector of length 2 containing a coefficient and exponent of at least one of the number as expressed in exponential notation, the numerical value as expressed in exponential notation. The representation of the numerical value may comprise a vector of length k formed by applying k weakly monotonic functions with overlapping dynamic ranges to at least one of the number, the numerical value.

The desired output may comprise at least one of: a translation, a highlighting, a diagnosis, a likelihood of an outcome, an indication of a contraindication.

The desired output may comprise at least one of a direction of change, a detection of normality, a detection of abnormality, a predictive value, a request for validation, an amount of a change, an indication of whether a value is within a predetermined interval, an indication of whether a value is within a variable interval, a comparison of two numbers.

The natural language data set may comprise medical information. The natural language data set may comprise a clinician's text notes.

Certain embodiments provide an apparatus for training a model to process a natural language data set comprising processing circuitry configured to: receive training data comprising natural language data; obtain pre-processed training data by: assigning a common number token to each number in the training data, wherein the common number token is a fixed indicator that does not depend on the value of each number; assigning a respective numerical value to each token in the training data, wherein the numerical value is zero or null or a default value if the token is not a number, and the numerical value comprises or is based on the value of the number if the token is a number; perform an embedding procedure on the tokens of the pre-processed data set to obtain respective embedding vectors for at least some of the tokens; for each of the embedding vectors, obtain an extended embedding vector by appending a representation of the numerical value assigned to the token for that embedding vector to obtain an extended embedding vector; and train a model to process the extended embedding vectors to obtain a desired output.

The trained model may comprise a neural network. The training of the model may comprise training the model to compare numbers expressed in natural language text.

The training of the model may comprise training the model to determine whether a number expressed in natural language text belongs to an interval. The interval may be variable. The interval may depend on contextual information in the text.

The model may learn to process numerical information without the model being provided with rules or templates for processing numerical information.

Certain embodiments provide an apparatus for training a model to process a natural language data set comprising processing circuitry configured to: receive training data comprising natural language data; train a model to learn values for numbers in the training data and to pass the values for the numbers to an inference system. Certain embodiments provide a method for preprocessing data for inputting to a neural network, comprising: receive a text data including numerical information, separate the text data into a text data not including numerical information and a data only including numerical information, transform the text data not including numerical information into a first data, transform the data only including numerical information into a second data, generate a vector data based on the first and second data.

Certain embodiments provide a system comprising a processing circuitry configured to: receive a text data including numerical information, separate the text data into a text data not including numerical information and a data only including numerical information, transform the text data not including numerical information into a first data, transform the data only including numerical information into a second data, generate a vector data based on the first and second data, output the vector data as a training data for neural network.

Whilst particular circuitries have been described herein, in alternative embodiments functionality of one or more of these circuitries can be provided by a single processing resource or other component, or functionality provided by a single circuitry can be provided by two or more processing resources or other components in combination. Reference to a single circuitry encompasses multiple components providing the functionality of that circuitry, whether or not such components are remote from one another, and reference to multiple circuitries encompasses a single component providing the functionality of those circuitries.

Whilst certain embodiments have been described, these embodiments have been presented by way of example only, and are not intended to limit the scope of the invention. Indeed the novel methods and systems described herein may be embodied in a variety of other forms. Furthermore, various omissions, substitutions and changes in the form of the methods and systems described herein may be made without departing from the spirit of the invention. The accompanying claims and their equivalents are intended to cover such forms and modifications as would fall within the scope of the invention.

The invention claimed is:

1. An apparatus comprising processing circuitry configured to pre-process text data for inputting to a trained model, the pre-processing comprising:
  receiving a set of text data, including numerical information, the set of text data comprising a plurality of tokens,
  wherein a first subset of the plurality of tokens are non-numerical tokens each of which does not comprise numerical information, and a second subset of the plurality of tokens are numerical tokens each comprising respective numerical information;
  transforming each non-numerical token of the first subset of the plurality of tokens into a respective encoding vector, wherein for each of the non-numerical tokens in the first subset the respective encoding vector is an encoding of the token;

transforming each numerical token of the second subset of the plurality of tokens into a respective encoding vector such that the encoding vector for each one of the numerical tokens of the second subset is identical to the encoding vector for every other one of the numerical tokens of the second subset;

assigning a respective numerical vector to each of the plurality of tokens, wherein each token in the second subset is assigned a respective numerical vector in dependence on the numerical information in said token; and extending the encoding vector for each token by the numerical vector for said token to obtain a respective extended embedding vector for each token, thereby obtaining a vector representation of the text data;

wherein the processing circuitry is further configured to input the vector representation to the trained model and to use the trained model to process the vector representation to obtain a desired output.

2. An apparatus according to claim 1, wherein each token in the first subset is assigned a common default numerical vector, such that each one of the tokens in the first subset is assigned the same numerical vector as each other one of the tokens in the first subset.

3. An apparatus according to claim 1, wherein each token comprises a respective word, word-piece, group of words, number, or symbol.

4. An apparatus according to claim 1, wherein the extending of the encoding vectors and numerical vectors comprises, for each token, appending the numerical vector for said token to the encoding vector for said token.

5. An apparatus according to claim 1, wherein each numerical vector comprises at least one of a) to d):
a) a fixed length vector comprising or representing the numerical information;
b) a vector of length 1 comprising or representing the numerical information;
c) a vector of length 2 comprising a mantissa and exponent that comprise or represent the numerical information;
d) a vector of length k formed by applying k weakly monotonic functions with overlapping dynamic ranges to the numerical information.

6. An apparatus according to claim 1, wherein the trained model comprises a neural network.

7. An apparatus according to claim 1, wherein the trained model is trained to approximate at least one mathematical operation.

8. An apparatus according to claim 1, wherein the desired output comprises at least one of a comparison of two or more numbers in the text data; a determination of whether a number in the text data belongs to an interval; a comparison of a number in the text data to a target value.

9. An apparatus according to claim 1, wherein the desired output comprises at least one of an assessment of a subject's condition; a chance of survival, an assessment of contraindications; a diagnosis; a prediction; a likelihood of an outcome; a summary of the text data; a determination of whether a number in the text data is normal; a determination of whether a number in the text data is abnormal.

10. An apparatus according to claim 1 wherein the text data comprises clinical notes and wherein the numerical information comprises at least one of laboratory data, symptom data, vital signs data, dosage data, measurement data, genomic data.

11. An apparatus according to claim 1, wherein the processing circuitry is further configured to display at least part of the text data to a user, and to highlight at least one number in the display of the text data in dependence on at least one output of the trained model.

12. An apparatus according to claim 1, wherein the vector representation is configured to capture a natural ordering of numbers.

13. A method comprising:
receiving a vector representation of training text data, the vector representation comprising a respective encoding vector and numerical vector for each of a plurality of tokens in the training text data wherein a first subset of the plurality of tokens are non-numerical tokens each of which does not comprise numerical information, and a second subset of the plurality of tokens are numerical tokens each comprising respective numerical information;

transforming each non-numerical token of the first subset of the plurality of tokens into a respective encoding vector, wherein for each of the non-numerical tokens in the first subset the respective encoding vector is an encoding of the token;

transforming each numerical token of the second subset of the plurality of tokens into a respective encoding vector such that the encoding vector for each one of the numerical tokens of the second subset is identical to the encoding vector for every other one of the numerical tokens of the second subset; and using the vector representation of the training text data to train a model to produce a desired output when provided with a further vector representation of a target text, wherein the desired output is dependent on numerical information in the target text; and inputting the further vector representation to a trained model and using the trained model to process the further vector representation to obtain the desired output.

14. A method of pre-processing text data for inputting to a trained model, the method comprising:
receiving a set of text data including numerical information, the set of text data comprising a plurality of tokens,
wherein a first subset of the plurality of tokens are non-numerical tokens each of which does not comprise numerical information, and a second subset of the plurality of tokens are numerical tokens each comprising respective numerical information;

transforming each non-numerical token of the first subset of the plurality of tokens into a respective encoding vector, wherein for each of the non-numerical tokens in the first subset the respective encoding vector is an encoding of the token;

transforming each numerical token of the second subset of the plurality of tokens into a respective encoding vector such that the encoding vector for each one of the numerical tokens of the second subset is identical to the encoding vector for every other one of the numerical tokens of the second subset;

assigning a respective numerical vector to each of the plurality of tokens, wherein each token in the second subset is assigned a respective numerical vector in dependence on the numerical information in said token;

extending the encoding vector for each token by the numerical vector for said token to obtain a respective extended embedding vector for each token, thereby obtaining a vector representation of the text data; and inputting the vector representation to the trained model and using the trained model to process the vector representation to obtain a desired output.

15. An apparatus comprising processing circuitry configured to:
receive a vector representation of a set of text data, wherein the vector representation has been obtained by pre-processing the set of text data, the pre-processing comprising:
receiving the set of text data, wherein the set of text data includes numerical information, the set of text data comprises a plurality of tokens, wherein a first subset of the plurality of tokens are non-numerical tokens each of which does not comprise numerical information, and a second subset of the plurality of tokens are numerical tokens each comprising respective numerical information;
transforming each non-numerical token of the first subset of the plurality of tokens into a respective encoding vector, wherein for each of the non-numerical tokens in the first subset the respective encoding vector is an encoding of the token;
transforming each numerical token of the second subset of the plurality of tokens into a respective encoding vector such that the encoding vector for each one of the numerical tokens of the second subset is identical to the encoding vector for every other one of the numerical tokens of the second subset;
assigning a respective numerical vector to each of the plurality of tokens, wherein each token in the second subset is assigned a respective numerical vector in dependence on the numerical information in said token; and
extending the encoding vector for each token by the numerical vector for said token to obtain a respective extended embedding vector for each token, thereby obtaining a vector representation of the text data; and
inputting the vector representation to a trained model and using the trained model to process the vector representation to obtain a desired output.

16. A method comprising:
receiving a vector representation of a set of text data, wherein the vector representation has been obtained by pre-processing the set of text data, the pre-processing comprising:
receiving the set of text data, wherein the set of text data includes numerical information, the set of text data comprises a plurality of tokens, wherein a first subset of the plurality of tokens are non-numerical tokens each of which does not comprise numerical information, and a second subset of the plurality of tokens are numerical tokens each comprising respective numerical information;
transforming each non-numerical token of the first subset of the plurality of tokens into a respective encoding vector, wherein for each of the non-numerical tokens in the first subset the respective encoding vector is an encoding of the token;
transforming each numerical token of the second subset of the plurality of tokens into a respective encoding vector such that the encoding vector for each one of the numerical tokens of the second subset is identical to the encoding vector for every other one of the numerical tokens of the second subset;
assigning a respective numerical vector to each of the plurality of tokens, wherein each token in the second subset is assigned a respective numerical vector in dependence on the numerical information in said token; and
extending the encoding vector for each token by the numerical vector for said token to obtain a respective extended embedding vector for each token, thereby obtaining a vector representation of the text data; and
inputting the vector representation to a trained model and using the trained model to process the vector representation to obtain a desired output.

17. An apparatus comprising processing circuitry configured to:
receive a vector representation of training text data, the vector representation comprising a respective encoding vector and numerical vector for each of a plurality of tokens in the training text data wherein a first subset of the plurality of tokens are non-numerical tokens each of which does not comprise numerical information, and a second subset of the plurality of tokens are numerical tokens each comprising respective numerical information;
transform each non-numerical token of the first subset of the plurality of tokens into a respective encoding vector, wherein for each of the non-numerical tokens in the first subset the respective encoding vector is an encoding of the token;
transform each numerical token of the second subset of the plurality of tokens into a respective encoding vector such that the encoding vector for each one of the numerical tokens of the second subset is identical to the encoding vector for every other one of the numerical tokens of the second subset;
use the vector representation of the training text data to train a model to produce a desired output when provided with a further vector representation of a target text, wherein the desired output is dependent on numerical information in the target text; and
inputting the further vector representation to a trained model and using the trained model to process the further vector representation to obtain the desired output.

* * * * *